US011044978B2

(12) United States Patent
Malle et al.

(10) Patent No.: US 11,044,978 B2
(45) Date of Patent: Jun. 29, 2021

(54) METHOD FOR STRAIGHTENING KERATINOUS FIBERS USING HEATING MEANS AND AN AROMATIC COMPOUND

(71) Applicant: L'Oreal, Paris (FR)

(72) Inventors: Gérard Malle, Villiers S/Morin (FR); Philippe Barbarat, Bois-Colombes (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/806,300

(22) Filed: Mar. 2, 2020

(65) Prior Publication Data

US 2020/0205541 A1 Jul. 2, 2020

Related U.S. Application Data

(60) Continuation of application No. 13/942,249, filed on Jul. 15, 2013, now abandoned, which is a division of application No. 12/301,900, filed as application No. PCT/FR2007/000871 on May 23, 2007, now abandoned.

(60) Provisional application No. 60/814,554, filed on Jun. 19, 2006.

(30) Foreign Application Priority Data

May 24, 2006 (FR) .................................... 0651910

(51) Int. Cl.
| | | |
|---|---|---|
| A61Q 5/04 | (2006.01) | |
| A45D 7/06 | (2006.01) | |
| A61K 8/368 | (2006.01) | |
| A61K 8/69 | (2006.01) | |
| A61K 8/41 | (2006.01) | |
| A61K 8/365 | (2006.01) | |
| A61K 8/42 | (2006.01) | |
| A61K 8/35 | (2006.01) | |
| A61K 8/34 | (2006.01) | |

(52) U.S. Cl.
CPC ............... *A45D 7/06* (2013.01); *A61K 8/347* (2013.01); *A61K 8/35* (2013.01); *A61K 8/365* (2013.01); *A61K 8/368* (2013.01); *A61K 8/415* (2013.01); *A61K 8/42* (2013.01); *A61K 8/69* (2013.01); *A61Q 5/04* (2013.01); *A61K 2800/24* (2013.01)

(58) Field of Classification Search
None
See application file for complete search history.

(56) References Cited

U.S. PATENT DOCUMENTS

| | | | |
|---|---|---|---|
| 3,847,165 A | 11/1974 | Patel et al. | |
| 4,198,558 A | 4/1980 | Benty | |
| 4,278,659 A | 7/1981 | Breuer | |
| 5,046,516 A | 9/1991 | Barradas | |
| 5,597,140 A | 1/1997 | McGee | |
| 5,641,477 A | 6/1997 | Syed et al. | |
| 8,765,107 B2 | 7/2014 | Philippe et al. | |
| 2003/0133898 A1 | 7/2003 | Philippe | |
| 2004/0000319 A1 | 1/2004 | Carballada et al. | |
| 2004/0180016 A1 | 9/2004 | Buck | |
| 2004/0265256 A1 | 12/2004 | Samain et al. | |
| 2005/0196368 A1 | 9/2005 | Laurent et al. | |
| 2006/0127337 A1* | 6/2006 | Radisson | A61K 8/43 424/70.2 |
| 2007/0218027 A1 | 9/2007 | Nguyen et al. | |
| 2009/0139537 A1 | 6/2009 | Malle et al. | |

FOREIGN PATENT DOCUMENTS

| | | | |
|---|---|---|---|
| CA | 1315204 C | 3/1993 | |
| EP | 1475075 B1 | 11/2004 | |
| EP | 1532963 A1 | 5/2005 | |
| EP | 1661551 A2 * | 5/2006 | ............... A61K 8/49 |
| EP | 1661551 A2 | 5/2006 | |
| FR | 2829925 A1 | 3/2003 | |
| GB | 1076420 A | 7/1967 | |
| JP | 2000-229819 A | 8/2000 | |
| JP | 2001-213741 A | 8/2001 | |
| NL | 6410355 | 3/1965 | |
| WO | 01/64171 A2 | 9/2001 | |
| WO | 02/03937 A2 | 1/2002 | |
| WO | 02/085317 A1 | 10/2002 | |

OTHER PUBLICATIONS

FR 2829925 (abstract) (Year: 2003).*
International Search Report for counterpart Application No. PCT/FR2007/000871, dated Oct. 16, 2007.
Wong, M., et al., "Mechanism of hair straightening," J. Soc. Cosmet. Chem., vol. 45, (Nov./Dec. 1994), pp. 347-352.
Non-Final Office Action for copending U.S. Appl. No. 13/942,249, dated Jan. 15, 2015.
Final Office Action for copending U.S. Appl. No. 13/942,249, dated Apr. 21, 2015.
Non-Final Office Action for copending U.S. Appl. No. 13/942,249, dated Jun. 9, 2015.
Final Office Action for copending U.S. Appl. No. 13/942,249, dated Jan. 15, 2016.
Non-Final Office Action for copending U.S. Appl. No. 13/942,249, dated Sep. 30, 2016.

(Continued)

*Primary Examiner* — Jyothsna A Venkat

(74) *Attorney, Agent, or Firm* — The Marbury Law Group, PLLC

(57) ABSTRACT

The invention concerns a method for straightening keratinous fibers including: (i) a step of applying on the keratinous fibers a hair straightening composition containing at least one polyhydroxylated aromatic compound, (ii) a step of increasing the temperature of the keratinous fibers, using heating means, to a temperature ranging between 110 and 250° C.

9 Claims, No Drawings

(56) References Cited

OTHER PUBLICATIONS

Final Office Action for copending U.S. Appl. No. 13/942,249, dated Jul. 14, 2017.
Non-Final Office Action for copending U.S. Appl. No. 13/942,249, dated Feb. 25, 2019.
Final Office Action for copending U.S. Appl. No. 13/942,249, dated Sep. 3, 2019.

* cited by examiner

METHOD FOR STRAIGHTENING KERATINOUS FIBERS USING HEATING MEANS AND AN AROMATIC COMPOUND

CROSS REFERENCE TO RELATED APPLICATION

This application is a continuation of U.S. patent application Ser. No. 13/942,249, filed Jul. 15, 2013, now abandoned, which is a division of U.S. patent application Ser. No. 12/301,900, filed Aug. 19, 2010, now abandoned, which is a national stage entry of International Application No. PCT/FR2007/000871, filed May 23, 2007, which claims priority to French Patent Application No. 0651910, filed May 24, 2006, and claims the benefit of priority to U.S. Provisional Application No. 60/814,554, filed Jun. 19, 2006, all of which are incorporated herein by reference in their entireties.

The invention relates to a process for relaxing keratin fibres with a heating means and at least one polyhydroxylated aromatic compound.

The relaxing process according to the invention is performed without using any reducing agent or lanthionizing agent. It does not include any reducing or lanthionization step.

According to the invention, the term "keratin fibres" means fibres of human or animal origin such as head hair, bodily hair, the eyelashes, wool, angora, cashmere or fur. Although the invention is not limited to particular keratin fibres, reference will nevertheless be made more particularly to head hair.

According to the invention, the term "relaxing" covers the relaxing, straightening or uncurling of Caucasian or African hair.

The term "heating means" means any means for heating keratin fibres to a temperature of at least 110° C., such as heating irons, for example flat or round irons, microwave generators or sources of infrared radiation.

Two techniques are used for permanently reshaping the hair. They are based on cleavage of the disulfide covalent bonds present in keratin (cystine):

the first consists, in a first stage, in performing this opening of the disulfide bonds using a composition containing a reducing agent, and then, after having preferably rinsed the hair, in reconstituting the said disulfide bonds in a second stage, by applying to the hair, which has been placed under tension beforehand with rollers or the like or shaped or straightened out by other means, an oxidizing composition also known as a fixer, so as to give the head of hair the desired shape. This technique makes it possible either to make the hair wavy or to relax it, uncurl it or straighten it out;

the second consists in performing a "lanthionization" operation using a composition containing a base belonging to the hydroxide family. This leads to replacement of the disulfide bonds (—CH2-S—S—CH2-) with lanthionine bonds (—CH2-S—CH2-). This lanthionization operation involves two consecutive chemical reactions:

the first reaction consists of a beta-elimination on cystine brought about by a hydroxide ion, leading to the cleavage of this bond and to the formation of dehydroalanine:

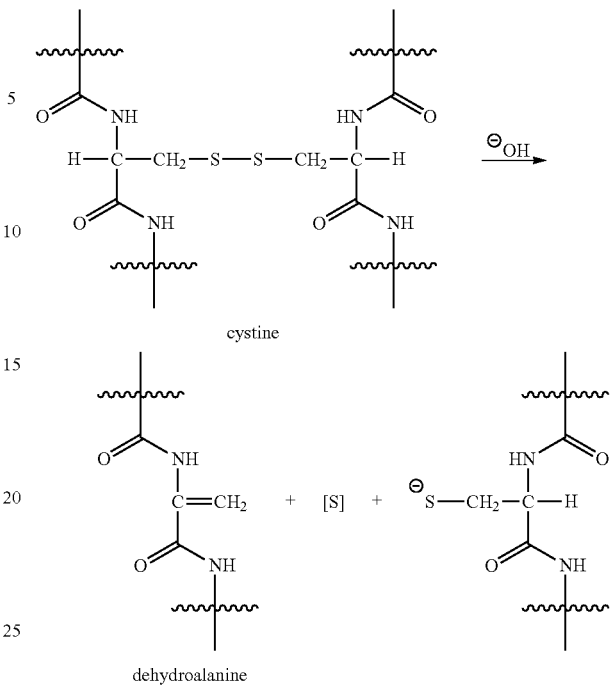

the second reaction is a reaction of dehydroalanine with a thiol group. Specifically, the double bond of the dehydroalanine formed is a reactive double bond. It can react with the thiol group of the cysteine residue that has been released to form a new bond referred as a lanthionine bridge or bond or residue.

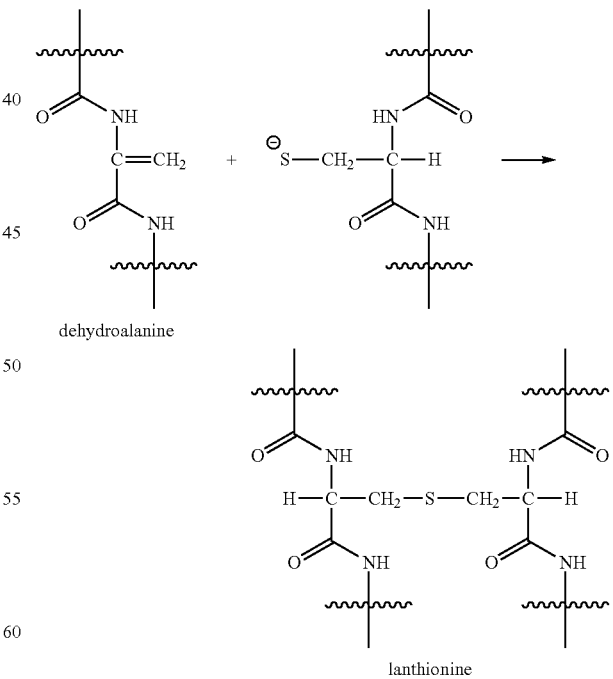

Relative to the first technique using a reducing agent, this lanthionization technique does not require a fixing step, since the formation of the lanthionine bridges is irreversible. It is thus performed in a single step and makes it possible either to make the hair wavy, or to relax it, uncurl or straighten it out. However, it is mainly used for relaxing naturally curly hair.

For the first technique, the reducing compositions generally used for the first step of a permanent-waving or hair-relaxing operation contain thiols, sulfites or bisulfites as reducing agent. These agents are generally used in essentially aqueous medium at concentrations of between 0.5 and 1 M to obtain good opening of the disulfide bonds. Among the thiols, those commonly used are thioglycolic acid, cysteamine, glyceryl monothioglycolate, thiolactic acid and cysteine. Thioglycolic acid is particularly efficient at reducing the disulfide bonds of keratin at alkaline pH, especially in the form of ammonium thioglycolate, and constitutes the product most frequently used in permanent waving ("hair waving"). It has been found, however, that thioglycolic acid must be used in sufficiently basic medium (in practice at a pH of between 8.5 and 9.5) if curling of satisfactory intensity is to be obtained. Besides the drawback of releasing an unpleasant odour requiring the use of more or less efficient fragrances to mask the odours, the use of a thiol at alkaline pH also results in degradation of the fibre and most particularly in impairment of artificial colorations.

Sulfites or bisulfites are mainly used for relaxing the hair. They have drawbacks similar to those of thiols, with lower efficacy.

Thiols and sulfites (or bisulfites) also have the drawback of having poor stability in aqueous solution.

In general, the durability of the reshaping effects obtained with thiols and sulfites by reduction of disulfides following by fixing is judged to be very much lower than that which may be obtained via the lanthionization technique.

For the second technique, the compositions generally used to perform lanthionization contain as base a hydroxide such as sodium hydroxide, guanidinium hydroxide or lithium hydroxide. These lanthionization active agents, which allow opening of the disulfide bonds via a beta-elimination mechanism, are generally used as a water-oil emulsion at concentrations of between 0.4 and 0.6 M, by leaving them to act generally for 10 to 15 minutes at room temperature. Sodium hydroxide remains the agent most frequently used. Guanidinium hydroxide is now the preferred compound for many compositions. These two hydroxides, sodium hydroxide and guanidinium hydroxide, are the two main agents used for the relaxing or uncurling of naturally curly hair. They have several advantages over ammonium thioglycolate and sulfites, in particular the absence of unpleasant odour, the fact that only one operating step is required (shorter treatment time) and much greater durability and efficacy of reshaping of the hair.

However, these hydroxides have the major drawback of being caustic. This causticity affects the scalp by causing irritation, which is occasionally severe. This may be partially remedied by applying beforehand to the scalp fatty protective cream often referred to as a "base" or "base cream", the word "base" in this case not having the meaning of a basic agent in the chemical sense. When the protective cream is combined with the hydroxide in a single composition, it is generally referred to as "no-base", as opposed to the above name. This "no-base" technique is preferred.

The causticity of hydroxides also affects the state of the hair by firstly giving it a coarse feel and secondly making it much more brittle, this brittleness possibly going as far as crumbling or breaking or even dissolution of the hair if the treatment is prolonged. In certain cases, hydroxides also cause decoloration of the natural colour of the hair.

Formulations containing sodium hydroxide are generally referred to as "lye relaxers" and those not containing it are referred as "no-lye relaxers".

The main relaxing formulations known as "no-lye" relaxers use guanidinium hydroxide. Since guanidinium hydroxide is unstable, it is generated at the time of use by mixing guanidinium carbonate and a source of sparingly soluble hydroxide such as calcium hydroxide. The reaction between these two compounds leads to the formation of guanidinium hydroxide and calcium carbonate, which precipitates in the composition. The presence of this precipitate makes the final rinsing of the hair much more difficult and leaves mineral particles on the hair and the scalp, which give it a coarse feel and an unaesthetic appearance resembling dandruff. The recent success of guanidinium hydroxide ("no-lye") over sodium hydroxide ("lye") appears to arise from better relaxing efficacy and better skin tolerance. However, these techniques using bases of the hydroxide family remain very aggressive to the hair and the scalp and require very strict control of the duration of application to avoid excessive irritation and impairment of the hair that may go as far as breakage. This aggressiveness arising from the causticity of hydroxides is justification for not using these hair lanthionization compositions for permanent waving (hair waving), but solely for hair straightening or hair relaxing.

Furthermore, hydroxides are known to be good agents for hydrolysing amide functions (cf. for example March's Advanced Organic Chemistry, 5th edition, Wiley Interscience, New York, "Hydrolysis of Amides" page 474 et seq.), which thus lead to cleavage of peptide bonds by direct nucleophilic attack. It is thus probable that the observed impairments of the hair and of keratin materials in the broad sense are largely due to partial hydrolysis of the amide bonds of keratin.

There is thus a real need for relaxing compositions that are markedly less aggressive to the hair.

Various studies have been conducted in order to overcome both the drawbacks of reducing agents (first technique) and/or those of hydroxides (second technique).

Thus, many reducing agents have been proposed to replace thioglycolic acid, but thioglycolic acid in the form of ammonium thioglycolate remains both the reference compound and the compound most widely used in cosmetic formulations, not only for shaping but also for straightening the hair.

It has also been proposed in numerous patents to combine common reducing agents (thiols, sulfites or bisulfites) with urea or alkyl ureas to reduce the irritation and damage caused to the hair, not only for shaping but also for relaxing. Mention will be made, for example, of:
  patent application CA 1315204, which describes a composition containing ammonium thioglycolate (5.5-11.5%) and urea or a monoalkyl urea (1-3%) for shaping the hair,
  U.S. Pat. No. 3,847,165, which describes a composition containing ammonium thioglycolate (1.2-1.4 M) and urea (2.0-2.7 M) for shaping the hair at an acidic pH,
  patent application NL 6410355, which describes a composition containing a sulfite (0.8-1.5 M) and urea (0.6-3.0 M) for shaping and relaxing the hair,
  patent application JP 2000/229 819, which describes a composition containing a sulfite or bisulfite (0.5-15%), urea (0.5-15%) and an alcohol (ethanol and/or isopropanol, 1-30%) for shaping and relaxing the hair.

It has also been proposed in numerous patents to combine hydroxides, serving as lanthionization active agent, with certain additives generally serving to protect the hair. Mention will be made, for example, of:
- patent application WO 2002/003 937, which describes a composition containing C3-C5 monosaccharides,
- patent application WO 2001/064 171, which describes a composition containing complexing agents,
- U.S. Pat. No. 5,641,477, which describes a composition containing a hydrogenated starch hydrolysate,
- patent application WO 02/085 317, which describes a composition containing organic nucleophiles that react during the second step with the dehydroalanine formed with hydroxides, to give new bridges.

Although all these proposals lead to more or less pronounced improvements, they are not able to sufficiently reduce the damage associated with the very causticity of hydroxides.

As indicated previously, the use of reducing agents leads to poor durability of the relaxing or straightening of the hair and the use of hydroxides, on account of their causticity, limits their use in the field of hair relaxing.

The use of resorcinol at a concentration of 40% and at a pH of 7 for relaxing the hair has been reported by M. Wong et al.: M. Wong, G. Vis-surel, and J. Epps J. Soc. Cosmet. Chem. (1994), 45, 347-352. However, the tests that we have performed under these conditions on naturally curly African hair do not relax it, but lead, at the very best, to slight uncurling.

After considerable studies, it has now been discovered, entirely surprisingly and unexpectedly, that hair can be durably relaxed by combining the action of a polyhydroxylated aromatic compound and of a means of heating to a temperature above 110° C. Excellent results in terms of relaxing, cosmetic properties of the hair and fibre integrity are thus obtained.

Without being bound by theory, the Applicant considers that there is a combined action, on the keratin fibres, of a polyhydroxylated aromatic compound and of a heating means, which allows the fibres to be efficiently and durably relaxed.

The Applicant has found that it is possible to overcome the drawbacks of the prior art and to satisfy the abovementioned objectives by performing a process for relaxing keratin fibres, comprising:
- a step of applying to the keratin fibres a hair-relaxing composition containing at least one polyhydroxylated aromatic compound, the pH of the composition being less than or equal to 9,
- a step of raising the temperature of the keratin fibres, using a heating means, to a temperature of between 110 and 250° C., the polyhydroxylated aromatic compound not being chosen from:
4,5-diamino-2,6-dihydroxypyrimidine, and
2,4-dihydroxypyrimidine-5-carboxylic acid.

Thus the invention relates to a process for relaxing keratin fibres, comprising:
- a step of applying to the keratin fibres a hair-relaxing composition containing at least one polyhydroxylated aromatic compound, the pH of the composition being less than or equal to 9,
- and then a step of raising the temperature of the keratin fibres, using a heating means, to a temperature of between 110 and 250° C., the polyhydroxylated aromatic compound not being chosen from:
4,5-diamino-2,6-dihydroxypyrimidine,
2,4-dihydroxypyrimidine-5-carboxylic acid,
2,4-dihydroxy-6-methylpyrimidine,
dihydroxyorotic acid, and
2,4,5-trihydroxypyrimidine.

Advantageously, the temperature is raised using a heating means to a temperature of between 120° C. and 220° C. and more advantageously between 140° C. and 220° C.

Preferably, the said composition is applied to wet keratin fibres.

A step intended to remove the excess composition, for example using a towel, may also be introduced between the step of applying the composition and the step of raising the temperature.

Definition of the polyhydroxylated aromatic compounds of general formula (I):

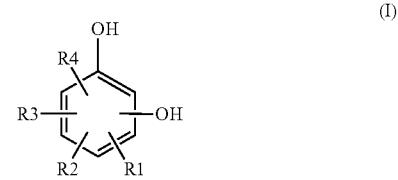

in which:
R1, R2, R3 and R4 represent, independently of each other:
H, F, Cl, Br, OH, OCH$_3$, OEt, CHO, COCH$_3$, COOH, CH$_2$NH$_2$, CH$_2$CH$_2$NH$_2$, CH$_2$OH, CH$_2$CH$_2$OH, CH$_2$COCH$_3$, CH$_2$COOH, CH$_2$CH$_2$COOH, CH$_2$CONH$_2$, CHOH—CH$_2$OH, —CH(NH$_2$)COOH, NHCOCH$_3$, COCH$_2$CH$_3$, CONH$_2$
or alternatively a linear or branched C1-C5 alkyl radical when the two OH radicals are in a meta position and when R1, R2 and R3 represent a hydrogen atom, R4 may also represent NH$_2$,
and the stereoisomers, organic or mineral salts and solvates thereof.

Preferred compounds of formula (I):
catechol
resorcinol
4-methylcatechol
3-methylcatechol
2-methylresorcinol
5-methylresorcinol
4-methylresorcinol
pyrogallol
1,2,4-trihydroxybenzene
phloroglucinol
3-fluorocatechol
4-fluorocatechol
4-fluororesorcinol
2,3-dihydroxybenzaldehyde
3,4-dihydroxybenzaldehyde
2,4-dihydroxybenzaldehyde
3,5-dihydroxybenzaldehyde
4-ethylcatechol
4-ethylresorcinol
2,5-dimethylresorcinol
4,5-dimethylresorcinol
2,4-dimethyl-1,3-benzenediol
3,4-dihydroxybenzylamine
3,5-dihydroxybenzylamine
3-methoxycatechol
5-methylpyrogallol
3,4-dihydroxybenzyl alcohol
5-methoxyresorcinol 2,4,6-trihydroxytoluene
3,5-dihydroxybenzyl alcohol
2-methoxyresorcinol
5-methylpyrogallol
4-methoxyresorcinol
3,5-dihydroxytoluene monohydrate
4-chlorocatechol
3-chlorocatechol
4-chlororesorcinol
2-chlororesorcinol
3',4'-dihydroxyacetophenone
2',3'-dihydroxyacetophenone
2',6'-dihydroxyacetophenone
2',4'-dihydroxyacetophenone
3',5'-dihydroxyacetophenone
2,6-dihydroxy-4-methylbenzaldehyde
3-isopropylcatechol
4-isopropylcatechol
4-propylresorcinol
2,4-dihydroxy-1,3,5-trimethylbenzene
3,4-dihydroxybenzamide
3,5-dihydroxybenzamide
2,6-dihydroxybenzamide
2,4-dihydroxybenzamide
3-hydroxytyramine
2,3-dihydroxybenzoic acid
3,4-dihydroxybenzoic acid
2,4-dihydroxybenzoic acid
2,6-dihydroxybenzoic acid
3,5-dihydroxybenzoic acid
2,3,4-trihydroxybenzaldehyde
2,4,6-trihydroxybenzaldehyde
3,4,5-trihydroxybenzaldehyde
2,4,5-trihydroxybenzaldehyde
2-(3,4-dihydroxyphenyl)ethanol
2,4,6-trihydroxy-1,3-dimethylbenzene
2,6-dihydroxy-4-methylbenzyl alcohol
2-fluoro-3,4-dihydroxybenzaldehyde
3,4-dihydroxy-6-fluorobenzaldehyde
2-methoxyphloroglucinol
3,5-dihydroxyanisole hydrate
4-aminoresorcinol hydrochloride
2-aminoresorcinol hydrochloride
5-aminobenzene-1,3-diol hydrochloride
phloroglucinol dihydrate
3',4'-dihydroxypropiophenone
3,4-dihydroxyphenylacetone
(2,3-dihydroxyphenyl)acetone
2',4'-dihydroxypropiophenone
2',4'-dihydroxy-3'-methylacetophenone
(2,4-dihydroxyphenyl)acetone
(3,5-dihydroxyphenyl)acetone
2,6-dihydroxy-4'-methylacetophenone
4-tert-butylcatechol
4-N-butylresorcinol
2,4-diethyl-1,3-benzenediol
3,4-dihydroxyphenylacetamide
3-hydroxyacetaminophen
2',3',4'-trihydroxyacetophenone
3,4-dihydroxyphenylacetic acid
2,3-dihydroxy-4-methoxybenzaldehyde
3,4-dihydroxy-5-methoxybenzaldehyde
2',3',4'-trihydroxyacetophenone
2',4',6'-trihydroxyacetophenone
3,5-dihydroxy-4-methylbenzoic acid
2,6-dihydroxy-4-methylbenzoic acid
2,4-dihydroxy-6-methylbenzoic acid
3,5-dihydroxyphenylacetic acid
2-ethyl-5-methoxybenzene-1,3-diol
3,4,5,-trihydroxybenzamide
4-amino-3,5-dihydroxybenzoic acid
2,3,4-trihydroxybenzoic acid
2,3,4-trihydroxybenzoic acid
gallic acid
2,4,6-trihydroxybenzoic acid
3,4-dihydroxyphenyl glycol
1,2-dihydroxy-4,5-dimethoxybenzene
3,5-dihydroxyacetophenone monohydrate
3,4-dihydroxybenzoic acid monohydrate
3,4,5-trihydroxybenzaldehyde
hexahydroxybenzene
3,5-dihydroxybenzylamine hydrochloride
4,6-diaminoresorcinol hydrochloride
4,5-dichlorocatechol
3,5-dichlorocatechol
4,6-dichlororesorcinol
2',4'-dihydroxy-3'-methylpropiophenone
1-(3-ethyl-2,6-dihydroxyphenyl)ethan-1-one
3-(3,4-dihydroxyphenyl)propionic acid
(2,3,4-trihydroxyphenyl)acetone
(2,4,5-trihydroxyphenyl)acetone
(3,4,5-trihydroxyphenyl)acetone
2',6'-dihydroxy-4'-methoxyacetophenone
1-(2,6-dihydroxy-3-methoxyphenyl)ethan-1-one
3(2,4-dihydroxyphenylpropionic acid
2,4-dihydroxy-3,6-dimethylbenzoic acid
(2,3,4-trihydroxyphenyl)acetone
(2,4,5-trihydroxyphenyl)acetone
(2,4,6-trihydroxyphenyl)acetone
(3,4,5-trihydroxyphenyl)acetone
3,4-dihydroxymandelic acid
5-hydroxyisovanillic acid
3,4,5-trihydroxybenzamide hydrate
4-bromocatechol
and the stereoisomers, organic or mineral salts and solvates thereof.

Particularly preferred compounds of formula (I):
resorcinol
2-methylresorcinol
5-methylresorcinol
4-methylresorcinol
pyrogallol
1,2,4-trihydroxybenzene
4-ethyl resorcinol
2,5-dimethylresorcinol
4,5-dimethylresorcinol
2,4-dimethyl-1,3-benzenediol
3,4-dihydroxybenzylamine
3,5-dihydroxybenzylamine
5-methylpyrogallol
3,4-dihydroxybenzyl alcohol
5-methoxyresorcinol
2,4,6-trihydroxytoluene
3,5-dihydroxybenzyl alcohol
2-methoxyresorcinol
5-methylpyrogallol
4-methoxyresorcinol
3,5-dihydroxytoluene monohydrate
4-propylresorcinol
2,4-dihydroxy-1,3,5-trimethylbenzene
3,4-dihydroxybenzamide
3,5-dihydroxybenzamide
2,6-dihydroxybenzamide
2,4-dihydroxybenzamide 3-hydroxytyramine
2,3-dihydroxybenzoic acid
3,4-dihydroxybenzoic acid
2,6-dihydroxybenzoic acid
3,5-dihydroxybenzoic acid
2-(3,4-dihydroxyphenyl)ethanol
2,4,6-trihydroxy-1,3-dimethylbenzene
2,6-dihydroxy-4-methylbenzyl alcohol
2-methoxyphloroglucinol
3,5-dihydroxyanisole hydrate
4-aminoresorcinol hydrochloride
2-aminoresorcinol hydrochloride
5-aminobenzene-1,3-diol hydrochloride
phloroglucinol dihydrate
2,4-diethyl-1,3-benzenediol
3,4-dihydroxyphenylacetamide
3,4-dihydroxyphenylacetic acid
3,5-dihydroxy-4-methylbenzoic acid
2,6-dihydroxy-4-methylbenzoic acid
2,4-dihydroxy-6-methylbenzoic acid
3,5-dihydroxyphenylacetic acid
2-ethyl-5-methoxybenzene-1,3-diol
3,4,5-trihydroxybenzamide
4-amino-3,5-dihydroxybenzoic acid
3,4-trihydroxybenzoic acid
gallic acid
2,4,6-trihydroxybenzoic acid
DL-3,4-dihydroxyphenyl glycol
1,2-dihydroxy-4,5-dimethoxybenzene
3,4-dihydroxybenzoic acid monohydrate
hexahydroxybenzene
3,5-dihydroxybenzylamine hydrochloride
sodium γ-resorcylate
sodium β-resorcylate
4,6-diaminoresorcinol hydrochloride
3-(3,4-dihydroxyphenyl)propionic acid
2,4-dihydroxy-3,6-dimethylbenzoic acid
DL-3,4-dihydroxymandelic acid
hydroxyisovanillic acid
3,4,5-trihydroxybenzamide acid hydrate
gallic acid monohydrate
and the stereoisomers, organic or mineral salts and solvates thereof.

Working Concentrations:

The working molar concentration is advantageously between 1 and 8 M, more advantageously between 1 and 4 M and even more advantageously between 1.5 and 3 M.

The working pH is preferably less than or equal to 7.

The compositions according to the invention are either in the form of an aqueous solution or in the form of a thickened cream so as to keep the hair as straight as possible. These creams are prepared in the form of "heavy" emulsions.

These compositions contain at least one polyhydroxylated aromatic compound of formula (I) and/or mixtures of several polyhydroxylated aromatic compounds of formula (I) in all proportions.

Advantageously, the compositions of the invention contain the polyhydroxylated aromatic compound as sole hair-relaxing active agent.

For the purpose of improving the cosmetic properties of keratin fibres or to attenuate or avoid their degradation, the composition used according to the invention may also comprise one or more additional cosmetic active agents.

Generally, the said additional cosmetic active agent(s) represent(s) from 0.01% to 30% and preferably from 0.1% to 10% by weight relative to the total weight of the cosmetic composition.

Generally, the composition applied to the keratin fibres is applied in an amount of from 0.05 to 20 g and preferably from 0.1 to 10 g of composition per gram of dry keratin fibre.

After applying the composition, and before raising the temperature of the keratin fibres using a heating means, the said composition may be left to act, generally for 30 seconds to 60 minutes and preferably 5 to 45 minutes.

The process according to the invention includes, after the step of applying the composition, a step of raising the temperature of the keratin fibres, using a heating means, to a temperature of between 110° C. and 250° C.

Advantageously, an iron is used as heating means.

For the purposes of the present invention, the term "iron" means a device for heating keratin fibres that places the said fibres and the heating device in contact.

The end of the iron that comes into contact with the hair generally having two flat surfaces. These two flat surfaces may be metallic. They may be smooth or crinkled.

As examples of irons that may be used in the process according to the invention, mention may be made of flat irons of any type, and in particular, in a non-limiting manner, those described in U.S. Pat. Nos. 5,957,140 and 5,046,516.

The iron may be applied by successive separate touches of a few seconds, or by gradually moving or sliding it along the locks.

Preferably, in the process according to the invention, the iron is applied by continuous movement from the root to the end, in one or more passes.

The process according to the invention may also include an additional step of partial predrying of the keratin fibres before the step of raising the temperature, so as to avoid substantial evolution of steam that might burn the stylist's hands and the individual's scalp. This predrying step may take place, for example, using a hairdryer, a hood or alternatively by drying in the open air.

The invention also relates to a kit comprising at least:
one heating means that affords a temperature of between 110 and 250° C.,
one hair-relaxing composition containing at least one polyhydroxylated aromatic compound, the pH of the composition being less than or equal to 9, the polyhydroxylated aromatic compound not being chosen from:
4,5-diamino-2,6-dihydroxypyrimidine, and
2,4-dihydroxypyrimidine-5-carboxylic acid.

Advantageously, in the kit, the hair-relaxing composition contains at least one polyhydroxylated aromatic compound of formula (I) as defined above.

The invention may be understood more clearly with the aid of the non-limiting examples that follow, which constitute preferential embodiments of the compositions according to the invention.

EXAMPLE 1

A simplified hair-relaxing composition is prepared, containing resorcinol at a concentration of 8 M in water, as hair-relaxing active agent. This composition is applied to naturally curly African hair for 15 minutes at a temperature of 40° C., and the hair is then rapidly towel-dried.

Lock-by-lock straightening of the head of hair is then performed using a flat iron heated to 180° C., for 10 to 15 seconds. The hair is efficiently relaxed and feels soft.

EXAMPLE 2

A simplified hair-relaxing composition is prepared, containing resorcinol at a concentration of 4 M in water, as hair-relaxing active agent. This composition is applied to naturally curly African hair for 15 minutes at a temperature of 40° C., and the hair is then rapidly towel-dried.

Lock-by-lock straightening of the head of hair is then performed using a flat iron heated to 180° C., for 10 to 15 seconds. The hair is efficiently relaxed and feels soft.

EXAMPLE 3

A simplified hair-relaxing composition is prepared, containing resorcinol at a concentration of 2 M in water, as hair-relaxing active agent. This composition is applied to naturally curly African hair for 25 minutes at a temperature of 40° C., and the hair is then rapidly towel-dried.

Lock-by-lock straightening of the head of hair is then performed using a flat iron heated to 180° C., for 10 to 15 seconds. The hair is efficiently relaxed and feels soft.

The invention claimed is:

1. A process for relaxing keratin fibers, comprising:
applying to the keratin fibers a hair-relaxing composition comprising a polyhydroxylated aromatic compound, wherein the pH of said hair relaxing composition is less than or equal to 9; and
heating the keratin fibers to a temperature ranging from 110° C. to 250° C.;
wherein the polyhydroxylated aromatic compound is gallic acid.

2. The process according to claim 1, wherein the keratin fibers are heated to a temperature ranging from 120° C. to 220° C.

3. The process according to claim 1, wherein the keratin fibers are heated to a temperature ranging from 140° C. to 220° C.

4. The process according to claim 1, wherein the hair-relaxing composition is applied to wet keratin fibers.

5. The process according to claim 1, wherein the keratin fibers are partially predried.

6. The process according to claim 1, wherein the molar concentration of gallic acid ranges from 1 to 8 M.

7. The process according to claim 1, wherein the molar concentration of gallic acid ranges from 1 to 4 M.

8. The process according to claim 1, wherein the molar concentration of gallic acid ranges from 1.5 to 3M.

9. The process according to claim 1, wherein the pH of the hair relaxing composition is less than or equal to 7.

* * * * *